United States Patent [19]

Walker et al.

[11] Patent Number: 4,656,205

[45] Date of Patent: Apr. 7, 1987

[54] MANUFACTURE OF POLYMERIC BEADS

[75] Inventors: John R. Walker, Halifax; John R. Stockwell, Bradford, both of United Kingdom

[73] Assignee: Allied Colloids Ltd., England

[21] Appl. No.: 673,975

[22] Filed: Nov. 23, 1984

[30] Foreign Application Priority Data

Nov. 25, 1983 [GB]  United Kingdom ................. 8331546
Aug. 10, 1984 [GB]  United Kingdom ................. 8420397

[51] Int. Cl.⁴ .............................................. C08F 2/20
[52] U.S. Cl. ................................... 523/201; 524/458; 524/460; 524/819; 524/827; 524/832; 524/833; 524/836; 525/902; 526/318.4; 526/318.45; 252/8.552
[58] Field of Search ............... 524/458, 460, 819, 827, 524/833, 836, 832; 526/318.4, 318.45; 424/19, 22; 525/227, 241, 902; 428/402; 585/12, 950; 166/304; 523/201

[56] References Cited

U.S. PATENT DOCUMENTS

| | | | |
|---|---|---|---|
| 3,906,087 | 9/1975 | Sim et al. | 424/22 |
| 4,178,361 | 12/1979 | Cohen et al. | 424/22 |
| 4,344,431 | 8/1982 | Yolles | 604/892 X |
| 4,411,754 | 10/1983 | Kaetsu et al. | 424/22 X |
| 4,588,640 | 5/1986 | Matlach | 523/207 X |

OTHER PUBLICATIONS

Chem. Abstracts, 94:214516n.

*Primary Examiner*—Joseph L. Schofer
*Assistant Examiner*—F. M. Teskin
*Attorney, Agent, or Firm*—Lawrence Rosen

[57] ABSTRACT

Beads comprising a polymeric matrix containing a releasable lipophilic compound are made by precipitating the compound from solution within the matrix. Beads may be made by forming a homogeneous blend of the compound in lipophilic polymerizable material and subjecting the blend to bead polymerization while the blend is dispersed as beads in an aqueous medium containing hydrophilic polymerization stabilizer. The lipophilic compound may be a behenyl ester wax inhibitor or other reagent useful downhole or for other purposes and preferably has a relatively high melting point. The polymerizable material preferably dissolves the lipophilic compound and may include acrylic acid, methacrylic acid or other hydrophilic polymerizable material.

16 Claims, No Drawings

MANUFACTURE OF POLYMERIC BEADS

There are many instances where it would be desirable to provide slow release of a lipophilic reagent from polymeric beads. Coacervation techniques from what can be considered to be capsules of polymer surrounding the bead and this is not entirely satisfactory for some applications. It is known to provide a polymeric matrix containing a releasable lipophilic reagent but it can be rather difficult to make such beads containing a suitable distribution of reagent and that will give adequate controlled release properties of the reagent. For instance, the reagent may diffuse from the matrix too quickly or not at all.

Another problem with such beads is that it can be difficult to make them by bead (suspension) polymerisation because of the difficulty of maintaining the beads in suspension in the aqueous medium during the polymerisation, especially in the presence of a reagent.

Another problem with such beads is that it is necessary that they should not stick together to an unacceptable extent during storage and, preferably, they should be relatively free flowing after storage. Many lipophilic reagents are oils and slow release of such reagents from beads during storage is likely to make the beads sticky such that they will stick together and will not be relatively free flowing. If a reagent is used that is a high melting solid, then it is difficult to incorporate this reagent uniformly into the beads.

Attempts at making such beads have been made (e.g. see Chemical Abstracts Vol. 94, 214516n) but these are not very satisfactory for very lipophilic reagents, especially those of value in hydrocarbon environments.

This invention relates to the manufacture of beads that comprise a polymeric matrix containing a substantially water insoluble lipophilic compound and that will provide a slow release of the lipophilic compound, or a reagent that can be liberated from the compound, into a fluid environment, and in particular to the production of such beads wherein the lipophilic compound is substantially uniformly distributed throughout the polymeric matrix. Thus the beads do not consist of a core consisting mainly or wholly of the lipophilic compound and a shell encapsulating the core and consisting mainly or wholly of the matrix but, instead, consist of a reasonably uniform distribution of the matrix polymer and the compound throughout most at least of the bead volume.

In one aspect of the invention the beads are made by a method comprising precipitating the lipophilic compound from solution within the beads to form a dispersion of the compound within the polymeric matrix.

The method of the invention is based on the surprising discovery that optimum slow release properties of the compound from the beads are achieved if the method of producing the beads, and the materials used in the production of the beads, are such that the compound is present as a dispersion within the polymeric matrix rather than as a solution. Thus, on a micro scale, the compound should be concentrated in small areas that, on a macro scale, are substantially uniformly distributed throughout the matrix. Thus the compound appears substantially uniformly distributed but is in fact present as a large number of concentrated deposits of the compound within the matrix.

By introducing the compound into the beads as a solution, it is possible to achieve substantially uniform distribution, on a macro scale, of the compound throughout the beads and then the precipitation of the compound from solution within the beads forms the dispersion of the compound within the matrix, or the non-uniform micro distribution of the compound that is desired for optimum results.

The solution is preferably formed at one temperature in a solvent for the compound and in which the compound is insoluble at a lower temperature and the beads are cooled to this lower temperature.

One method of the invention comprises swelling the beads by a swelling agent for the matrix, carrying the lipophilic compound into the swollen matrix as a solution in a solvent in which it is soluble at the prevailing temperature but is insoluble at a lower temperature, reducing the temperature to the lower temperature and thereby precipitating the compound within the matrix, and then evaporating, diffusing, or otherwise removing the solvent and the swelling agent.

The solvent for the lipophilic compound and the swelling agent for the matrix (if different from the solvent), will be chosen having regard to the particular matrix and lipophilic compounds being used. Often the solvent is selected from aliphatic or, preferably, aromatic hydrocarbons such as toluene and xylene, ketones such as methylethyl ketone and acetone, and esters such as ethyl acetate.

In a preferred process, the beads in which the compound is initially in solution are beads of polymerisable material that can be polymerised to form the polymeric matrix. The precipitation may then be associated with or follow the polymerisation and preferably is caused by the polymerisation.

The solution of the lipophilic compound in the polymerisable material may be formed with the aid of a cosolvent, that is to say an inert, non-polymerisable solvent but is preferably formed without a cosolvent, the lipophilic compound being soluble in the polymerisable material under the conditions of polymerisation.

According to another aspect of the invention, beads that comprise a polymeric matrix containing a substantially water insoluble lipophilic compound and that will provide a slow release of the lipophilic compound, or a reagent that can be liberated from the compound, into a fluid environment may be made by a method comprising forming a homogeneous blend of the lipophilic compound in lipophilic polymerisable material and subjecting the blend to bead polymerisation while the blend is dispersed as a substantially stable dispersion of beads in an aqueous medium containing a hydrophilic polymerisation stabiliser.

It is necessary for the lipophilic compound to be present as a homogenous blend in the polymerisable material in order that the compound is substantially uniformly distributed throughout the polymeric matrix. The process conditions, and materials used, are preferably such that the homogeneous blend takes the form of a solution of the lipophilic compound in the polymerisable material but the polymerisable material is preferably such that, in the final beads, the lipophilic compound is not in solution in the polymeric matrix but is instead present as a microdispersion in the polymeric matrix, as discussed above.

The lipophilic compound is preferably a material that is solid at ambient temperatures and so has a melting point above 25° C., preferably above 50° C., for instance 50° to 80° C. By choosing such a material as the lipophilic compound, the risk of the beads sticking together during storage is minimised.

Unfortunately, the choice of a high melting lipophilic compound increases the difficulties of providing a homogeneous blend of the compound in polymerisable material. These high melting compounds, and certain other lipophilic compounds, tend to be insoluble in the lipophilic polymerisable material at 25° C. Although a cosolvent can be used to provide the solution or other homogeneous blend, this is generally undesirable.

In a preferred method of the invention, the lipophilic compound is substantially immiscible with the polymerisable material at 25° C. but is miscible with it at an elevated temperature and the blending of the reagent with the polymerisable material is conducted at the said elevated temperature in the substantial absence of non-polymerisable solvent for the reagent. In particular, the method is preferably carried out by blending the reagent with the aqueous medium at the said elevated temperature and then mixing into the resultant blend the polymerisable material under conditions such that the desired elevated temperature is maintained. Upon stirring the polymerisable material into the blend, the reagent will migrate into the polymerisable material and be held there when that material is polymerised. The said elevated temperature is generally above 50° C., typically 50° to 80° C.

The polymerisation is conducted as a bead polymerisation in aqueous medium containing a hydrophilic polymerisation stabiliser. Thus the homogeneous blend of lipophilic compound in polymerisable material is broken up into beads which are held in suspension in the aqueous medium as a result of the presence of the hydrophilic polymerisation stabiliser.

It is desirable that the bead size and shape of the final beads should be as uniform as possible and we find that improved results are obtained if the lipophilic polymerisable material includes some hydrophilic polymerisable material. Various hydrophilic monomers can be used. Suitable non-ionic hydrophilic monomers include hydroxyethyl methacrylate or other hydroxy alkyl (meth) acrylates. Cationic monomers include dialkyl aminoalkyl (meth) acrylates. It is usually preferred to use anionic monomers, generally an ethylenically unsaturated carboxylic monomer such as acrylic acid or, preferably methacrylic acid. A suitable amount is generally in the range of 1 to 10% by weight of polymerisable material.

We have found that properties of the beads, and in particular the release properties of the beads, are improved if a hydrophilic shell is formed on the beads. This shell may be applied onto the beads after formation but preferably is formed during polymerisation by migration of hydrophilic polymerisable material towards the surface of the beads during polymerisation. For this migration to occur, it is necessary for the hydrophilic polymerisable material to be highly hydrophilic, the material preferably being acrylic acid.

For optimising stability of the beads, the amount of hydrophilic monomer, generally methacrylic acid, is preferably in the range of 1 to 10% and for providing the optimum hydrophilic shell the amount of acrylic acid or other hydrophilic monomer is preferably also in the range 1 to 10% by weight. Although, in the invention, it is possible to achieve useful results using methacrylic acid alone or acrylic acid alone, preferably both are present, each in an amount of 1 to 10% by weight.

The lipophilic polymerisable material preferably consists mainly of acrylic alkyl ester or styrene or acrylonitrile or a mixture thereof. Suitable acrylic esters are alkyl acrylates and methacrylates where the alkyl group contains from 1 to 6 and preferably 1 to 3 carbon atoms. The ester is preferably a methacrylate and the preferred ester is methyl methacrylate.

The polymeric matrix preferably has a softening point as measured by a temperature-graded hot bar of above 30° C. and most preferably is above 60° C. It may be up to 200° C., often up to 120° C.

The polymer is preferably formed mainly of methyl methacrylate or a blend of methyl methacrylate (usually 50 to 90% by weight of the blend) and styrene.

Small amounts of other polymerisable monomers, for instance up to 40%, generally below 20% by weight and preferably below 10% by weight, may be included provided they do not deleteriously affect the properties of the polymer. As mentioned above, it is particularly preferred to include carboxylic monomers such as acrylic or methacrylic acid. Other suitable monomers include hydroxyalkyl acrylates and methacrylates, maleate esters, vinyl esters, and dialkylaminoalkylacrylates and methacrylates.

The polymer is preferably a linear polymer but if desired, cross linking monomers, such as glycol dimethacrylate, can be included in the polymerisable material to form a cross-linked polymer.

The lipophilic compound must be lipophilic in the sense that it must partition into the polymerisable phase in preference to the aqueous phase. Usually the solution of the compound in water at 25° C. is below 1%, preferably below 0.1% by weight, and preferably the solubility in the aqueous medium at the polymerisation temperature is below 1%, most preferably below 0.1%, by weight.

In the method of the invention, it is necessary to select the polymerisable material and the hydrophilic polymerisation stabiliser such that it does not react with the lipophilic compound, as any such reaction may destabilise the suspension and/or prevent release of the lipophilic compound from the beads during use. For instance if the lipophilic compound is an amino compound, it is generally desirable for the reaction system to be free of compound containing free carboxylic acid groups, because of the risk of reaction between the amino group and the carboxylic groups. For instance, any hydrophilic monomers and polymerisation stabiliser should generally be non-ionic or cationic.

Preferably a homogeneous blend is formed of the lipophilic compound and the monomer or monomers dispersed into the aqueous medium by stirring and polymerisation is initiated by using an oil soluble thermal initiator.

Polymerisation is conducted whilst maintaining the particles dispersed in the aqueous medium and results in the formation of a suspension of polymer beads each containing lipophilic compound uniformly dispersed or dissolved throughout the major part at least of the matrix. The beads may be filtered or otherwise separated from the aqueous medium and may be washed. Although the beads can be dried, it is often convenient to maintain them either damp or in the presence of excess aqueous medium.

The particle size is generally at least 10 microns and preferably at least 50, and usually at least 100, microns since small particles can be difficult to handle and to position permanently in their desired environment. The particle size is generally less than 2 mm and preferably less than 1 mm, since large particles also may be difficult to position in their desired environment. Best results are generally obtained with a particle size of from 0.2 to 1 mm. The particles are preferably substantially spherical.

The amount of lipophilic compound is generally at least 5% by weight of the total bead in order to maximise the amount of compound introduced into the desired location. It can be difficult to produce beads containing very high amounts of compound and so the amount is generally not more than 50%, and usually not more than 30%, by weight of the total beads. The preferred reagent amount is usually 10 to 30% by weight of the beads.

The lipophilic compound is preferably a reagent that is to be released from the beads into a fluid environment but may be a compound that will liberate such a reagent upon prolonged contact of the beads with the environment. For instance a water soluble reagent containing a basic nitrogen atom, for instance a biocide or corrosion inhibitor, may be incorporated into the beads as a lipophilic salt of such a reagent and this salt may decompose upon prolonged exposure of the beads to water in order to liberate the water soluble corrosion inhibitor or biocide. Generally, however, the lipophilic compound is intended to be released, chemically unchanged, from the beads in order to serve as a useful reagent in the fluid environment into which it is released.

It may be a pesticide or nutrient, for instance an insecticide, herbicide or other pesticidally active compound or it may be a nutrient that may be a source of trace elements or may be a fertiliser, or it may be other agriculturally or horticulturally useful compound that can be released slowly in damp air, for instance moist soil or humid air, or irrigation water.

The compound may be a corrosion inhibitor or biocide that is to be released into water. Preferably, however, the lipophilic compound is a compound that is soluble in refined or crude oil and preferably the environment into which it is to be released is a downhole, pipeline or other oil containing environment. Preferred lipophilic compounds for oil environments are selected from wax deposition inhibitors, pour point depressants, demulsifiers, scale inhibitors, corrosion inhibitors, biocides, ashless dispersants and antioxidants.

The invention is of particular value when the lipophilic compound is a wax deposition inhibitor. Suitable materials are described in U.S. Pat. Nos. 3,693,720 and 3,854,893 and particularly preferred materials are reaction products of an olefin and maleic anhydride with a long chain (typically $C_{16}$–$C_{28}$) aliphatic alcohols, most preferably the behenyl ester of alkenyl succinic anhydride having a molecular weight of from 3,000 to 10,000 formed by polymerising a $C_{22}$–$C_{28}$ alphaolefin with maleic anhydride.

The following are examples of the invention.

EXAMPLE 1

The behenyl half ester of a $C_{24}$–$C_{28}$ alkenyl succinic anhydride polymer produced generally according to the procedure set forth for preparation of Polymer B disclosed in U.S. Pat. No. 3,854,893 was supplied as a solution in toluene, and this solvent was evaporated to leave a waxy solid. This wax, i.e. the reagent, was insoluble in methyl methacrylate monomers at temperatures up to 50° C. A monomer solution containing the wax reagent was formed of 85 g methyl methacrylate, 5 g methacrylic acid and 10 g of the wax by heating all to 65° C., at which temperature the wax dissolved into the monomers. The resultant solution was then dispersed in 200 g water containing 3 g polyacrylic acid (molecular weight about 2 million) in a one liter enclosed vessel provided with a stirrer for controlled agitation of the contents within the vessel. Under constant agitation, 1 g of azodiisobutyronitrile as the polymerisation initiator was added. Suspension polymerisation was continued with constant agitation for two hours after which time the product within the vessel consisted of a suspension of small polymeric beads in the aqueous medium. These beads were separated from the aqueous medium, washed, allowed to cool to ambient temperature and dried to give free flowing beads of from 0.2 to 1 mm in diameter with 10% by weight of the waxy ester polymer reagent dispersed in the polymeric matrix.

Since the behenyl ester wax reagent is very soluble in hexane, to demonstrate the retardation of solubility by the invention the produced beads were stirred in hexane at 35° C. and the amount of wax released recorded. The following results were obtained. % of Total Wax Released at 35° C.

| | Time Hours |
|---|---|
| 40 | 1 |
| 42 | 2 |
| 45 | 3 |
| 49 | 4 |
| 53 | 5 |

EXAMPLE 2

When the above process was repeated using 10 g wax reagent (as above described), 5 g acrylic acid, 5 g methacrylic acid and 80 g methyl methacrylate followed by neutralisation with sodium hydroxide dispersion, the beads have a shell containing a high proportion of sodium polyacrylate and have slower release properties compared to the release properties of the beads in Example 1 when the polymerisate dispersion was similarly neutralised. In particular, after 5 hours at 35° C. in hexane as in Example 1, only 25% of the wax was released.

EXAMPLE 3

The process of Examples 1 and 2 can be repeated effectively when using 3 g low molecular weight hydroxyethyl cellulose (sold under the trade name "Natrosol" 250 LR) in place of the polyacrylic acid.

EXAMPLE 4

To demonstrate the value of providing the lipophilic compound in a micro-dispersion or precipitated form within the polymer, as opposed to solution or truly homogeneous form within the polymer, the process of Example 1 can be repeated using dibutyl phthalate (a plasticiser for the polymer) in place of the behenyl half ester. The plasticiser for the polymer will form a true solution. Comparison of the release properties of the beads containing the plasticiser with the release properties of the beads containing the behenyl ester demonstrates the great superiority of the beads containing the behenyl ester in that the plasticiser does not diffuse out of the beads into the hexane to any significant extent. The better diffusion of the behenyl ester seems to be because it is present as micro dispersion, as opposed to solution, in the polymeric matrix.

EXAMPLE 5

A solution of the behenyl ester used in Example 1 is formed freely in toluene at temperatures above 50° C.

but upon cooling such a solution the behenyl half ester is very liable to precipitate from the solution.

Beads of cross-linked polymethyl methacrylate may be soaked in such a solution at 50° C. for sufficient time to allow a high degree of swelling to occur, the beads may then be cooled to precipitate the behenyl half ester within the cross-linked matrix, and the toluene may then be allowed to evaporate from the beads. These beads are likely to carry a relatively high surface concentration of the behenyl half ester, as well as a substantially uniform (on a macro scale) distribution of the half ester throughout the polymeric matrix, but this coating is tolerable, especially since the high melting point of the behenyl half ester ensures that the beads are relatively free flowing despite the existance of the coating.

We claim:

1. A method of making beads that comprise a polymeric matrix formed from lipophilic polymerisable material and up to 40% of other polymerisable material and containing a substantially water insoluble lipophilic compound that will provide slow release of the lipophilic compound, or a reagent that can be liberated from the compound, into a fluid environment, and in which the lipophilic compound is insoluble in the polymerisable material at 25° C. and has a melting point greater than 25° C., the method comprising forming a homogeneous blend of the lipophilic compound in the polymerisable material in the substantial absence of nonpolymerisable solvent for said compound and at an elevated temperature greater than 25° C. at which the lipophilic compound is soluble in the lipophilic polymerisable material, and subjecting the blend to bead polymerisation while the blend is dispersed as a substantially stable dispersion of beads in an aqueous medium containing a hydrophilic polymerisation stabilizer.

2. A method according to claim 1 in which the homogeneous blend is a solution of the lipophilic compound in the polymerisable material and the lipophilic compound is in a micro dispersion in the polymeric matrix.

3. A method according to claim 1 in which the lipophilic compound is dissolved in the polymerisable material in the absence of cosolvent.

4. A method according to claim 1 in which the said elevated temperature is from 50° to 80° C.

5. A method according to claim 4 in which the homogeneous blend is a solution of the lipophilic compound in the lipophilic polymerisable material and the solution is formed by forming a mixture of the aqueous medium and the lipophilic compound at the said elevated temperature and then dispersing the polymerisable material into the mixture as beads while maintaining the mixture at the said elevated temperature and allowing the lipophilic compound to diffuse into the beads from the aqueous medium.

6. A method according to claim 1 in which the beads are stabilised during the polymerisation by incorporating hydrophilic polymerisable material with the lipophilic polymerisable material.

7. A method according to claim 6 in which the hydrophilic material is methacrylic acid in an amount of from 1 to 10% by weight of polymerisable material.

8. A method according to claim 1 in which a hydrophilic polymeric shell is formed on the beads during polymerisation by incorporating hydrophilic polymerisable material in the polymerisable material and by migration of this hydrophilic material to the surface of the beads during polymerisation.

9. A method according to claim 8 in which the hydrophilic polymerisable material is acrylic acid in an amount of from 1 to 10% by weight of the polymerisable material.

10. A method according to claim 1 in which the lipophilic compound has a melting point of at least 50° C.

11. A method according to claim 1 in which the polymeric matrix is formed from 80 to 99% by weight of lipophilic polymerisable material selected from acrylic alkyl esters, styrene and acrylonitrile and 1 to 20% by weight of polymerisable material is selected from hydrophilic monomers.

12. A method according to claim 1 in which the polymeric matrix is formed from 80 to 99% by weight of lipophilic polymerisable material selected from methyl methacrylate and a blend of methyl methacrylate with a lesser amount of styrene and 1 to 20% by weight of polymerisable hydrophilic monomer selected from acrylic acid and methacrylic acid.

13. A method according to claim 1 in which the polymeric matrix is formed from polymerisable material that consists of 80 to 99% by weight methyl methacrylate, 1 to 10% by weight methacrylic acid and 1 to 10%, by weight acrylic acid.

14. A method according to claim 1 in which the lipophilic compound is a wax inhibitor.

15. A method according to claim 14 in which the inhibitor is a behenyl ester of alkenyl succinic anhydride polymer having a molecular weight of 3,000 to 10,000.

16. A method of making beads that comprise a lipophilic matrix containing a substantially water insoluble, lipophilic, wax inhibitor and that will provide slow release of the wax inhibitor into a fluid environment, and in which the polymeric matrix has a softening point of 30 to 200 degrees C. as measured by a temperature graded hot bar and is formed by polymerisation of polymerisable material consisting of 80 to 99% by weight lipophilic monomer selected from methyl methacrylate and a blend of methyl methacrylate with a lesser amount of styrene and 1 to 20% by weight polymerisable hydrophilic monomer selected from acrylic acid and methacrylic acid, and the wax inhibitor is a behenyl ester of alkenyl succinic anhydride polymer having a molecular weight of 3,000 to 10,000 and is insoluble in the polymerisable material at 25 degrees C. but is soluble at 50 to 80 degrees C., and in which the method comprises forming a homogeneous blend of the wax inhibitor in the polymerisable material at a temperature of from 50 to 80 degrees C. and at which the wax inhibitor is soluble in the polymerisable material and subjecting the blend to bead polymerisation while the blend is dispersed as a substantially stable dispersion of beads in an aqueous medium containing a hydrophilic polymerisation stabiliser.

* * * * *